United States Patent [19]

Gegelys

[11] Patent Number: 4,643,726
[45] Date of Patent: Feb. 17, 1987

[54] INCONTINENCE INSERT

[75] Inventor: Anthony A. Gegelys, Somerset, N.J.

[73] Assignee: E. R. Squibb & Sons, Inc., Princeton, N.J.

[21] Appl. No.: 626,175

[22] Filed: Jun. 29, 1984

Related U.S. Application Data

[63] Continuation-in-part of Ser. No. 514,620, Jul. 18, 1983, abandoned.

[51] Int. Cl.⁴ .............................................. A61F 13/16
[52] U.S. Cl. ................................... 604/368; 604/378
[58] Field of Search ................ 604/368, 378, 383, 389

[56] References Cited

U.S. PATENT DOCUMENTS

| | | | |
|---|---|---|---|
| 2,699,170 | 1/1955 | Morin | 128/287 |
| 2,896,627 | 7/1959 | Harwood | 128/290 |
| 3,072,123 | 1/1963 | Davis | 128/284 |
| 3,183,910 | 5/1965 | Patterson | 128/290 |
| 3,211,147 | 10/1965 | Pherson et al. | 128/284 |
| 3,315,676 | 4/1967 | Cooper | 128/287 |
| 3,344,789 | 10/1967 | Arnold et al. | 128/287 |
| 3,431,911 | 3/1969 | Meisel | 128/287 |
| 3,563,242 | 1/1971 | Hedstrom | 604/378 |
| 3,570,492 | 3/1971 | Bettencourt | 128/290 |
| 3,654,929 | 4/1972 | Nillson et al. | 604/378 |
| 3,666,611 | 5/1972 | Joa | 161/147 |
| 3,707,430 | 12/1972 | Costanza et al. | 161/123 |
| 3,721,242 | 3/1973 | Krusko | 128/287 |
| 3,769,978 | 11/1973 | DeNight et al. | 128/287 |
| 3,868,287 | 2/1975 | Lewyckyj | 156/201 |
| 3,871,037 | 3/1975 | Willington | 5/91 |
| 3,886,941 | 6/1975 | Duane et al. | 604/378 |
| 3,888,257 | 6/1975 | Cook et al. | 604/378 |
| 3,890,974 | 6/1975 | Kozak | 604/368 |
| 3,897,784 | 8/1975 | Fitzgerald | 128/290 |
| 3,938,522 | 2/1976 | Repke | 128/287 |
| 4,002,171 | 1/1977 | Taft | 128/284 |
| 4,027,672 | 6/1977 | Karami | 128/284 |
| 4,041,949 | 8/1977 | Kozak | 128/287 |
| 4,055,180 | 10/1977 | Karami | 128/287 |
| 4,055,184 | 10/1977 | Karami | 128/287 |
| 4,085,754 | 4/1978 | Ness et al. | 128/287 |
| 4,093,765 | 6/1978 | Schmidt | 428/134 |
| 4,173,046 | 11/1979 | Gallagher | 604/378 |
| 4,232,674 | 11/1980 | Melican | 604/378 |
| 4,251,643 | 2/1981 | Harada et al. | 604/368 |
| 4,269,188 | 5/1981 | Nishizawa et al. | 604/378 |
| 4,282,874 | 8/1981 | Mesek | 604/389 |
| 4,372,309 | 2/1983 | Fowler | 128/284 |

FOREIGN PATENT DOCUMENTS 0004499  1/1979  Japan .................................. 604/368

Primary Examiner—John D. Yasko
Attorney, Agent, or Firm—Lawrence S. Levinson; Stephen B. Davis

[57] ABSTRACT

The hourglass-shaped insert includes a moisture permeable inner layer and a moisture impermeable layer enclosing a layer of moisture absorbent core material. Located between the cut-out leg sections of the insert and interposed between the inner layer and the absorbent material is a uni-directional moisture barrier layer and a wicking layer. The barrier layer is a laminate containing a polymer that expands when wetted and includes a plurality of apertures. Adhesive strips are mounted on the outer layer to releasably secure the insert to an undergarment.

9 Claims, 6 Drawing Figures

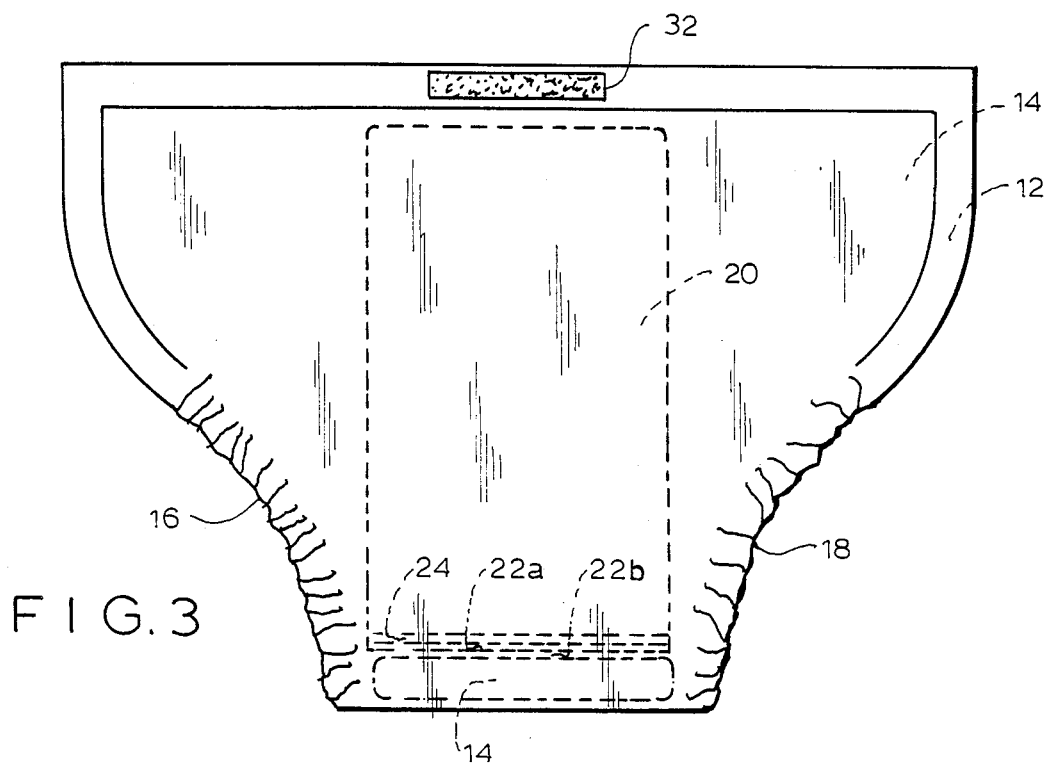
FIG. 3
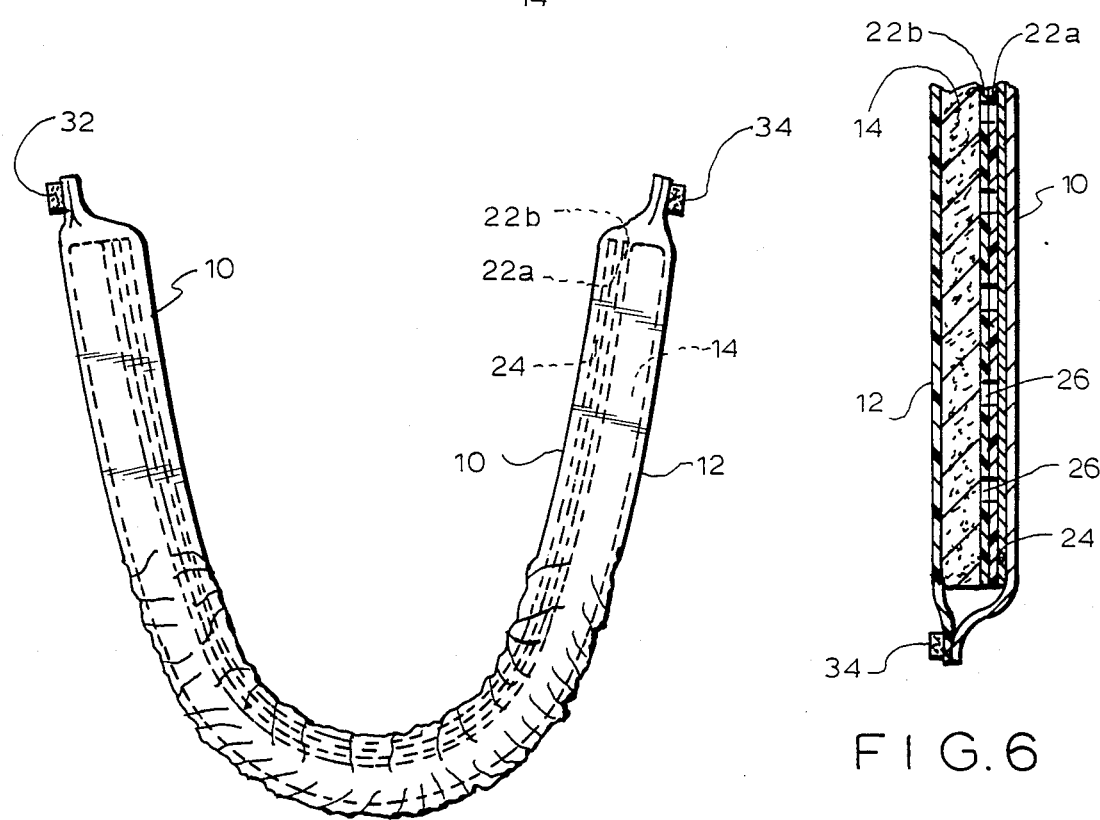
FIG. 4
FIG. 6

INCONTINENCE INSERT

RELATED APPLICATION

This application is a continuation-in-part of Ser. No. 514,620 filed on July 18, 1983, now abandoned.

BACKGROUND OF THE INVENTION

Many individuals, either due to advanced age or illness, are unable to control or restrain the natural discharge of waste material. Individuals who are incontinent with respect to liquid waste normally utilize an incontinent garment in the form of a brief or the like which has a pocket therein. Into the pocket is inserted a disposable moisture-absorbent pad which can be changed as necessary. The garment itself is normally washable, such that it can be used repeatedly. Individuals who are incontinent with respect to solid waste material normally have to utilize an adult version of a diaper which is fitted to their body contours and will contain excreted solid waste material.

In both cases, the garment or diaper may be a source of embarrassment to the adult individual because of the stigma involved in wearing such garments. Thus, while the use of such garments is intended to permit the incontinent individual to lead as normal a life as possible, the wearing of an incontinent garment or diaper may itself restrict some of the activities in which the individual would like to participate.

In addition, with respect to both incontinence garments which accept a removable pad and adult diapers, it is necessary that the garment or diaper be correctly fitted to the contours of the body of the individual. In particular, it is necessary that the garment or diaper fit snuggly around the waist and hips of the wearer in order to look and function properly. Accordingly, such garments and diapers have been provided, either in individual sizes to suit various sized individuals, or in a single size which is adjustable by means of elastic waistbands, snaps, or size adjusting adhesive tabs or the like to permit the individual the necessary adjustability.

While there are incontinence garments fabricated for use by individuals who cannot control liquid waste and other types of incontinence garments designed for use by individuals who cannot control solid waste, there are few garments which are comfortable and easy to change. The garments designed for use to absorb liquid waste are normally highly moisture-absorbent, but are incapable of effectively encapsulating solid waste.

OBJECTS OF THE INVENTION

It is, therefore, a prime object of the present invention to provide an incontinence insert designed for use in conjunction with conventional undergarments.

It is another object of the present invention to provide an incontinence insert which need not be sized to accomodate the contours of the wearer's body.

It is another object of the present invention to provide an incontinence insert which is highly effective in absorbing liquid waste, as well as encapsulating solid waste.

It is another object of the present invention to provide an incontinence insert which includes a uni-directional moisture barrier which permits liquid waste to be absorbed, but thereafter, prevents same from moving back towards the wearer, thereby preventing the insert from having an uncomfortable wet feel.

It is another object of the present invention to provide an incontinence insert which can be fabricated using standard manufacturing techniques.

It is a further object of the present invention to provide an incontinence insert composed of relatively inexpensive parts which function together reliably.

SUMMARY OF THE INVENTION

In accordance with the present invention, an insert is provided for use by incontinent individuals which is adapted to be situated in a conventional undergarment. The insert comprises a substantially hourglass-shaped body with cut-out sections to accomodate the legs of the individual. The body includes an inner layer of non-woven moisture permeable material, an outer layer of moisture impermeable material, and a layer of moisture absorbent core material. The inner layer and the outer layer are joined along the periphery of the body to enclose the absorbent layer. A centrally located portion, situated between the cut-out sections, is interposed between the inner layer and the absorbent core material. The central portion includes a uni-directional moisture barrier layer adjacent the absorbent core material and a moisture permeable wicking layer between the barrier layer and the inner layer. The barrier layer has a plurality of apertures therein. The apertures in the barrier layer facilitate the movement of liquid from the inner layer to the absorbent material. Adhesive means are mounted on the outer layer and adapted to releasably secure the insert to an undergarment.

The uni-directional barrier layer is a laminate of a "super absorbent" polymer and a base or carrier of paper or the like. Suitable commercially available "super absorbent" polymers include starches, acrylics, modified cellulose, gums and the like. The polymer material may be coated onto a paper base or sandwiched between layers of paper to form the laminate. The "super absorbent" polymer, once it becomes wet, will gel and expand. The barrier layer also includes a number of apertures extending through the barrier layer and spaced across the surface of the barrier layer. These apertures facilitate the movement of moisture from the moisture permeable inner layer, through the barrier layer, and into the moisture absorbent core material. As the polymer becomes wet and gels, it expands, thereby reducing the size of the apertures and preventing moisture from moving back through the barrier layer from the core material to the permeable inner layer which is in contact with the skin of the wearer. Thus, the apertured layer acts to retain moisture in the absorbent core material by functioning as a uni-directional moisture barrier.

The adhesive means comprises first and second adhesive strips situated proximate the ends of the body of the insert. These strips permit the insert to be snuggly anchored within the undergarment.

BRIEF DESCRIPTION OF THE INVENTION

FIG. 3 is a front view of the incontinence insert of the present invention;

FIG. 4 is a side view of the incontinence insert of the present invention;

FIG. 6 is a cross-sectional view of the incontinence insert of the present invention taken along line 6—6 of FIG. 2.

DETAILED DESCRIPTION OF THE INVENTION

Figure 1:
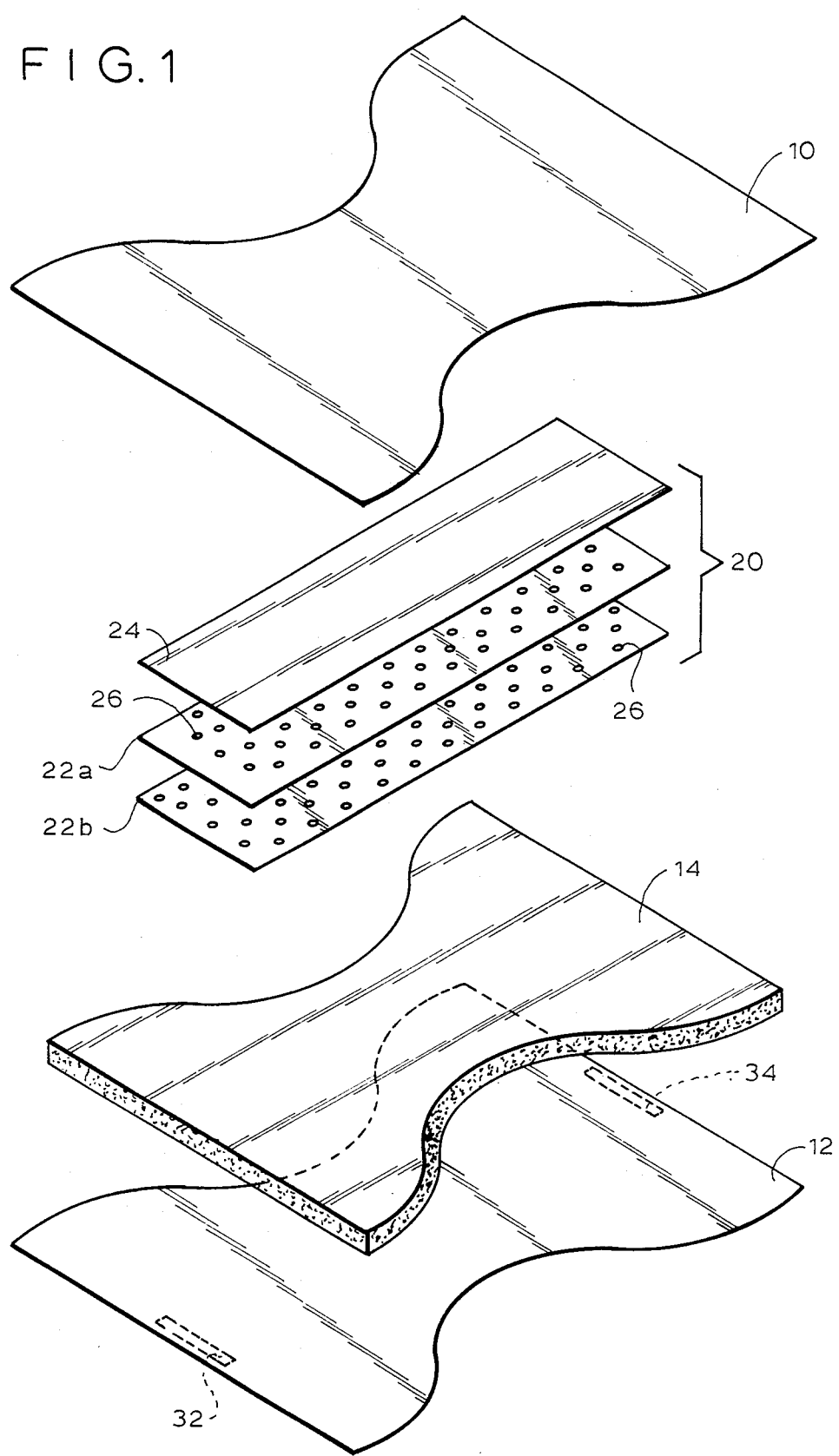
FIG. 1 is an exploded isometric view of the incontinence insert of the present invention.
Figure 2:
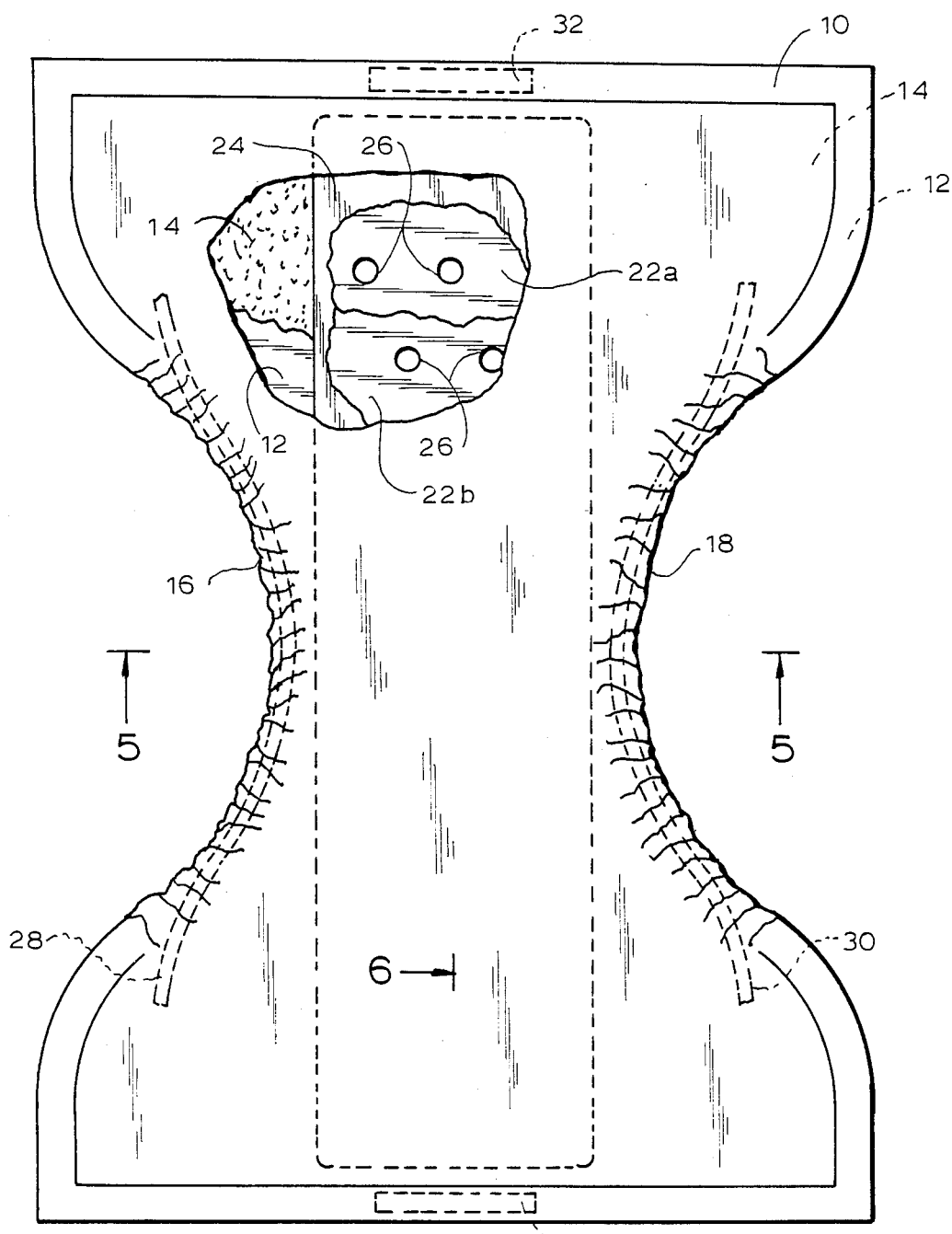
FIG. 2 is a top plan view of the incontinence insert of the present invention.
Figure 5:
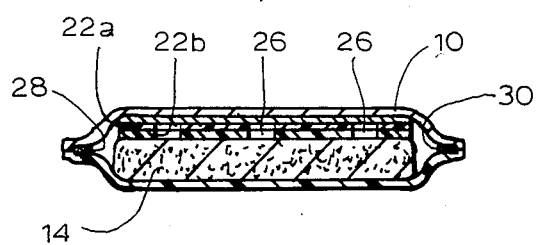
FIG. 5 is a cross-sectional view of the incontinence insert of the present invention taken along line 5—5 of FIG. 2.

The present invention relates to incontinence devices and, more particularly, to an incontinence insert designed for use with conventional undergarments in order to contain both liquid and solid waste material.

As shown in the drawings, the incontinence insert of the present invention has a substantially hourglass-shaped body formed of an hourglass-shaped inner layer 10 composed of a non-woven, moisture-permeable fabric, such as polyester, polypropylene, or rayon fibers, or the like which permit the passage of fluid therethrough. Inner layer 10 is attached to a similarly shaped outer layer 12 to enclose the remaining portions of the insert. Layer 12 is composed of a moisture impermeable plastic material such as polyethylene, polypropylene, or the like. The peripheries of inner layer 10 and outer layer 12 are affixed to each other by adhesive or the like so as to form an hourglass-shaped interior recess.

This recess is filled with a layer of moisture absorbent core material 14 that also has an hourglass shape, but is of dimensions slightly smaller than the dimensions of inner layer 10 or outer layer 12. The moisture absorbent core material is composed of fluffed wood pulp, which is preferred, tissue wadding, foams, non-wovens, batting or the like.

Situated between the semicircular cut-out portions 16 and 18 designed to accommodate the legs of the wearer, and extending along the vertical center line of the insert, from a point proximate one end thereof to a point proximate the other end thereof, is a generally rectangular portion 20. Portion 20 is formed of a uni-directional barrier layer 22 and a wicking layer 24. Layers 22 and 24 are situated between the moisture absorbent core material 14 and the interior surface of inner layer 10 with layer 22 adjacent the moisture core absorbent material 14 and layer 24 adjacent the interior surface of inner layer 10. Barrier layer 22 functions to retain liquid within material 14.

Uni-directional barrier layer 22 is of a planar, rectangular shape and is of substantially uniform thickness. The "super absorbent" polymer constituent of barrier layer 22 gels and expands when wet. Thus, this layer will act to block the transfer of moisture therethrough. Barrier 22, if formed of an uninterrupted laminate, would gradually restrict the amount of moisture passing therethrough and, finally, after being completely gelled and expanded, would effectively block any moisture from passing into moisture absorbent material 14.

To enhance the amount of fluid, i.e., urine, which can pass through uni-directional barrier layer 22, barrier layer 22 is provided with a large number of apertures 26. The shape, size, and number of apertures can be varied according to the gelling and expansion characteristics of the particular "super absorbent" polymer employed. As layer 22 gradually undergoes the transition which results in gelling and expanding, the swelling of the "super absorbent" polymer substantially decreases the size of the apertures. Thus, the passage of moisture through the barrier layer is gradually reduced, but much more gradually than if no apertures were present.

Accordingly, barrier 22 will act to retain moisture within the absorbent core material by permitting a substantial amount of moisture to pass through it to absorbent core layer 14, but, thereafter, preventing any substantial amount of liquid from passing from absorbent core layer 14 back through barrier layer 22 and wicking layer 24 to the moisture permeable inner layer 10 and, thus, back to the wearer. The result is that the top of the insert will be more comfortable to the wearer because it will not have a wet feel.

Uni-directional barrier layer 22 may be a single sheet of material, several sheets arranged so that the apertures 26 are aligned as note sheets 22a and 22b in the figures, or a single sheet bent or folded in such a manner that apertures 26 are aligned. Preferred materials for barrier layer 22 are a laminate containing a "super absorbent" starch polymer known as DWAL (trademark of Dow Chemical) and a laminate containing a "super absorbent" modified acrylic polymer known as Gelok 4000 (trademark of Gelok International).

Wicking layer 24 is of a moisture permeable material, preferably tissue paper, and it functions to more uniformly disperse the fluid, i.e., urine, passing through permeable inner layer 10 onto uni-directional barrier layer 22. Thus, wicking layer 24 assures that the "super absorbent" polymer component of barrier layer 22 will gel and expand more uniformly across the entire surface of layer 22.

The insert of the present invention is designed to be situated within a conventional undergarment. Cut-out portions 16 and 18 are each provided with an internal elastic strip 28, 30 which tends to gather the sections of inner layer 10 and outer layer 12 along the cut-out portions 16 and 18, such that the insert will fit snuggly around the inside of the legs of the wearer.

The exterior surface of outer layer 12 is provided with adhesive strips 32, 34 located proximate the edges of the body portion of the insert, as illustrated in FIGS. 3 and 4, to permit the insert to be securely anchored to the interior of the undergarment. Strips 32, 34 will prevent the insert from moving around within the undergarment and enhance the comfort thereof.

It will now be appreciated that the present invention is usable with conventional undergarments, and thereby eliminates the necessity of the use of an incontinence garment and pad combination, or an adult diaper and, accordingly, the stigma attached thereto. In addition, one size of insert fits all, thereby eliminating the necessity for different size garments to fit the hips and waist of the wearer.

The insert has a relatively large surface area and, therefore, is capable of effectively encapsulating solid waste material. In addition, the central portion of the insert is provided with a uni-directional moisture barrier such that moisture absorbent material can absorb a large amount of liquid without leaking back to the skin of the wearer, thereby creating an uncomfortable wet feeling.

It will now be appreciated that the structure of the insert of the present invention permits same to be used effectively to both absorb a large amount of liquid waste and, at the same time, has a large enough surface area to effectively encapsulate solid waste material. Thus, a single insert can be used for both purposes.

A preferred incontinence insert according to this invention is as follows. Liquid permeable inner layer 10 is a non-woven polyester or rayon material of from about 0.25 to about 2 ounces per square yard, most preferably at about 0.5 ounces per square yard. Liquid impermeable outer layer 12 is a polyethylene film of from about 0.5 mils to about 3 mils, most preferably at about 1 mil thickness. Wicking layer 24 is tissue material at from about 1 to about 3 mils, most preferably about 2 mils thick. Uni-directional barrier layer or layers 22 are preferably of sufficient thickness and include an amount of "super absorbent" polymer so as to absorb from about 30 to about 100 times its weight in urine. Apertures 26 are preferably dimensioned so as to occupy from about 15% to about 35% of the surface area, most preferably about 25% of the surface area, of barrier layer or layers 22 prior to contact with moisture. Moisture absorbent core material 14 is preferably a fluffed wood pulp of about 0.15 inches to about 1.5 inches thick, most preferably about 0.25 to about 0.5 inches.

What is claimed is:

1. An insert for use by incontinent individuals adapted to be situated in a conventional undergarment, the insert consisting of a substantially hourglass-shaped body with cut-out sections to accomodate the legs of the individual, said body consisting of an inner layer of non-woven moisture permeable polyester or rayon fiber, an outer layer of moisture impermeable polyethylene film, and a single layer of moisture absorbent fluffed wood pulp core material, said inner layer and said outer layer being joined along the periphery of said body to enclose said absorbent core material, a centrally located portion situated between said cut-out sections and interposed between said inner layer and said absorbent material, said portion consisting of a uni-directional barrier layer of substantially uniform thickness and a moisture permeable wicking layer of tissue material situated between said barrier layer and said inner layer, said barrier layer comprising a laminate containing a polymer that expands when wetted, said barrier layer having a plurality of apertures therethrough, said apertures having a given diameter prior to the expansion of said polymer to facilitate the passage of liquid through said barrier layer to said absorbent core material, the diameter of said apertures decreasing as said polymer expands so as to restrict the passage of liquid back through said barrier layer towards said permeable inner layer.

2. The insert of claim 1, further comprising adhesive means mounted on the outer layer and adapted to releasably secure said insert to an undergarment.

3. The insert of claim 1, wherein said non-woven moisture permeable polyester or rayon fiber is of from about 0.25 to about 2 ounces per square yard, said moisture impermeable polyethylene film is from about 0.5 mils to about 3 mils, said tissue wicking layer is from about 1 to about 3 mils, said moisture absorbent fluffed wood pulp core is from about 0.15 inches to about 1.5 inches, and said apertures constitute from about 15% to about 35% of the surface area of said uni-directional barrier layer prior to contact with moisture.

4. The insert of claim 3, wherein said barrier layer is a plurality of apertured sheets, said apertures being substantially aligned, each sheet being of substantially uniform thickness and comprising a laminate of a base or carrier and a polymer that expands when wetted.

5. The insert of claim 4, wherein said polymer is a starch polymer.

6. The insert of claim 4, wherein said polymer is an acrylic polymer.

7. The insert of claim 4, wherein said barrier layer is an apertured sheet of substantially uniform thickness folded one or more times such that the apertures are substantially aligned, said sheet comprising a laminate of a base or carrier and a polymer that expands when wetted.

8. The pad of claim 7, wherein said polymer is a starch polymer.

9. The pad of claim 7, wherein said polymer is an acrylic polymer.

* * * * *